United States Patent [19]

di Palma et al.

[11] Patent Number: 4,968,301
[45] Date of Patent: Nov. 6, 1990

[54] DISPOSABLE INFUSION DEVICE

[75] Inventors: Giorgio di Palma, Ramona; Victor L. Bartholomew, Escondido, both of Calif.

[73] Assignee: Imed Corporation, San Diego, Calif.

[21] Appl. No.: 305,972

[22] Filed: Feb. 2, 1989

[51] Int. Cl.⁵ .............................................. A61M 5/00
[52] U.S. Cl. .............................. 604/132; 128/DIG. 12
[58] Field of Search ............... 128/DIG. 12; 604/19, 604/126, 131–135, 123, 212, 214, 246, 249, 250

[56] References Cited

U.S. PATENT DOCUMENTS

| | | | |
|---|---|---|---|
| 7,816 | 12/1850 | Trotter. | |
| 1,895,623 | 1/1933 | Hewitt. | |
| 1,907,673 | 5/1933 | Rockwell. | |
| 2,222,869 | 11/1940 | Jencick | 103/150 |
| 2,471,796 | 5/1949 | Thiberg | 230/170 |
| 2,764,942 | 10/1956 | Guarnaschelli et al. | 103/38 |
| 2,791,195 | 5/1957 | Alden | 103/150 |
| 2,803,195 | 8/1957 | Lock | 103/152 |
| 2,930,324 | 3/1960 | Toulmin, Jr. | 103/53 |
| 3,023,750 | 3/1962 | Baron | 128/214 |
| 3,039,399 | 6/1962 | Everett | 103/150 |
| 3,080,825 | 3/1963 | Guarnaschelli et al. | 103/150 |
| 3,212,446 | 10/1965 | Golden et al. | 103/150 |
| 3,381,582 | 5/1968 | Golden | 91/47 |
| 3,412,906 | 11/1968 | Dinger | 222/183 |
| 3,416,461 | 12/1968 | McFarland | 103/150 |
| 3,468,308 | 9/1969 | Bierman | 128/214 |
| 3,469,578 | 9/1969 | Bierman | 128/214 |
| 3,496,437 | 2/1970 | Balson | 604/132 |
| 3,496,878 | 2/1970 | Hargest et al. | 103/152 |
| 3,506,005 | 4/1970 | Gilio et al. | 128/214 |
| 3,653,377 | 4/1972 | Rebold | 128/66 |
| 3,672,543 | 6/1972 | Roper et al. | 222/183 |
| 3,677,444 | 8/1972 | Merrill | 222/135 |
| 3,698,595 | 10/1972 | Gortz et al. | 220/63 |
| 3,738,538 | 6/1973 | Roper et al. | 222/183 |
| 3,791,557 | 2/1974 | Venus, Jr. | 222/105 |
| 3,796,356 | 3/1974 | Venus, Jr. | 222/212 |
| 3,876,115 | 4/1975 | Venus, Jr. et al. | 222/183 |
| 3,947,156 | 3/1976 | Becker | 417/437 |
| 3,961,725 | 6/1976 | Clark | 222/1 |
| 3,981,415 | 9/1976 | Fowler et al. | 222/95 |
| 3,993,069 | 11/1976 | Buckles et al. | 604/132 |
| 4,030,495 | 6/1977 | Virag | 604/123 |
| 4,058,123 | 11/1977 | May | 604/133 |
| 4,112,947 | 9/1978 | Nehring | 604/133 |
| 4,318,400 | 3/1982 | Peery et al. | 128/214 |
| 4,386,929 | 6/1983 | Peery et al. | 604/132 |
| 4,411,603 | 10/1983 | Kell | 417/479 |
| 4,419,096 | 12/1983 | Leeper et al. | 604/132 |
| 4,541,788 | 9/1985 | Nomura et al. | 417/471 |
| 4,573,883 | 3/1986 | Noon et al. | 417/394 |
| 4,636,197 | 1/1987 | Chu | 604/131 |
| 4,642,098 | 2/1987 | Lundquist | 604/126 |
| 4,734,092 | 3/1988 | Millerd | 604/67 |
| 4,769,008 | 9/1988 | Hessel | 604/132 |
| 4,772,263 | 9/1988 | Dorman et al. | 604/132 |
| 4,813,937 | 3/1989 | Vaillancourt | 604/131 |

FOREIGN PATENT DOCUMENTS 0114677 8/1984 European Pat. Off. ............. 604/19

OTHER PUBLICATIONS

Van Vlack, Elements of Material Science and Engineering 1985, pp. 227, 228, 613.
Throne, James L., "Modeling Plug-Assist Thermoforming", *Advances in Polymer Technology*, vol. 9, No. 4, 1989, pp. 309–320.

*Primary Examiner*—John D. Yasko
*Assistant Examiner*—Anthony M. Gutowski
*Attorney, Agent, or Firm*—Nydegger & Harshman

[57] ABSTRACT

A disposable IV infusion device for ambulatory patients comprises a disk-shaped cover plate and a disk-shaped impeller plate which are interconnected by a stretched membrane that joins the edge of the cover plate with the edge of the impeller plate. The effect of the membrane is to urge the plates into juxtaposition. A fluid port is formed on the cover plate for fluid communication through the port with a collapsible fluid chamber established between the plates. Fluid, when injected into the chamber between the plates, is subsequently expelled through the port for controlled infusion to a patient as the membrane pulls the plates toward each other to collapse the chamber.

3 Claims, 2 Drawing Sheets

DISPOSABLE INFUSION DEVICE

FIELD OF THE INVENTION

The present invention pertains to devices which are useful for infusing medical solutions to patients. More particularly, the present invention pertains to mechanically operated IV infusion pumps. The present invention is particularly, but not exclusively, useful as an IV infusion pump for therapy of ambulatory patients.

BACKGROUND OF THE INVENTION

Many devices have been proposed for infusing medical solutions to patients. Although these devices may be specifically engineered to optimized some particular aspect or feature of the infusion process, and thus be designed to function in quite different ways, their basic objective is the same. Namely, each device is intended to infuse fluids to a patient at an effectively constant rate over a specified interval of time to achieve volumetric accuracy in a sustained operation.

It will be appreciated that IV infusion therapy may be appropriate for various purposes in a wide variety of situations. Further, although many IV patients are bedridden, it may not always be necessary for the patient to remain lying down during infusion therapy. Indeed, but for limitations imposed by the infusion device being used, there may be no need for the patient to remain nonambulatory for the prolonged periods of time that may be necessary for the therapy. Accordingly, some IV devices have been specifically engineered and designed for use by ambulatory patients.

To be effective, operational IV infusion devices which can be carried by ambulatory patients need to satisfy several specific requirements. First, the device should be light weight and be easily carried by the patient. Further, the device should be simple to operate and easy to use. Additionally, the simplicity of the device will, hopefully, permit complete operation by the patient without assitance from medical staff personnel. Importantly, the device must operate within selected operational parameters which will ensure sufficient infusion accuracy to properly treat the particular ailment of the patient.

In order to reduce weight requirements, several IV infusion devices intended for use by ambulatory patients have avoided incorporating electronic components. Instead, they have relied on purely mechanical means for infusing fluids to the patient. One method is, of course, to rely on gravity to infuse fluids into the patient. A gravity means, however, can be cumbersome for the ambulatory patient. Alternatively, a stored energy device, such as a spring, may be used to impart a positive mechanical force on the fluid being infused. Perhaps more efficiently, such a positive force may be generated with an elastomeric material sucha as latex. These elastomeric materials are relatively light weight when compared with spring loaded devices and, accordingly, have some appeal. It happens, however, that the force which is generated by a stretched elastomeric material is substantially constant throughout only a part of the range of stretch given to the material. For operation outside this range, there is a nonlinear variable force response from the material which can cause an erratic pumping operation. Since it is desirable to have a constant force applied to the fluid, in order to maintain predictable fluid flow, if an elastomeric material is used to provide the impelling force for an IV infusion device it is preferable that the elastomeric material remain stretched in that part of the range of stretch where a substantially constant force results. Further, in order to avoid additional unpredictable nonlinearities, it is desirable that the elastomeric material providing the impelling force be stretched equally over the area of material generating the force.

In light of the above, it is an object of the present invention to provide a disposable IV infusion device for use by an ambulatory patient which uses an elastomeric material that is maintained in a stretched state during sustained operation to infuse fluids with a substantially constant force on the fluid. Another object of the present invention is to provide a disposable IV infusion device for use by an ambulatory patient which is light weight and easy to carry. Still another object of the present invention is to provide an IV infusion device for use by an ambulatory patient which is simple to operate and maintain and which can be reused if desired. Yet another object of the present invention is to provide an IV infusion device for use by an ambulatory patient which is relatively easy to manufacture and comparatively cost effective.

SUMMARY OF THE INVENTION

A novel IV infusion device for use by an ambulatory patient in accordance with the present invention comprises a substantially disk-shaped cover plate which is formed with a fluid port and an air vent. A hydrophobic barrier is incorporated with the air vent to prevent the flow of fluid from the device through the vent. The fluid port incorporates an actuating valve that permits opening of the normally closed fluid port, in accordance with the desires of the operator, to allow fluid flow through the port. A substantially disk-shaped impeller plate is provided and is connected with the cover plate by means of a stretchable membrane. Specifically, the stretched membrane interconnects the edge of the cover plate with the edge of the impeller plate. A substantially hollow cylindrical housing having a periphery is attached to the cover plate with the periphery of the housing engaged at the edge of the cover plate. As so connected, the housing is positioned in a surrounding relationship with the impeller plate. In order to prevent the contamination of medications by chemical interactions between the medications and the membrane, a liner may be disposed between the cover plate and the impeller plate to hold medications therebetween. Thus, with the liner periphery joined with the edge of the cover plate, the medications are effectively isolated from the membrane.

In the operation of the present invention, fluid is injected through the fluid port into the space between the cover plate and the linear. This causes a fluid chamber to form between the liner and cover plate which expands as long as fluid is being injected. Any gases, such as air, which may inadvertently be injected with the fluid into the fluid chamber are allowed to escape through the hydrophobic barrier and its associated air vent. With the expansion of the fluid chamber, the impeller plate is distanced from the cover plate and the elastomeric membrane is stretched. Once the desired amount of fluid has been injected into the chamber, the source of fluid may be removed from the fluid port and the actuating valve in the port will automatically be closed to confine fluid within the chamber. An IV line may subsequently be connected with the fluid port in fluid communication with the chamber. A fluid flow control device, such as a roller clamp, can then be associated with the IV line to either prevent fluid flow through the line or allow fluid flow through the line according to the desires of the operator. As fluid is allowed to flow through the IV tube, the stretched elastomeric membrane tends to urge the impeller plate toward the cover plate. This action collapses the fluid chamber to expel fluid from the fluid chamber through the fluid port, and this will continue until the elastomeric membrane brings the impeller plate into juxtaposed contact with the cover plate.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
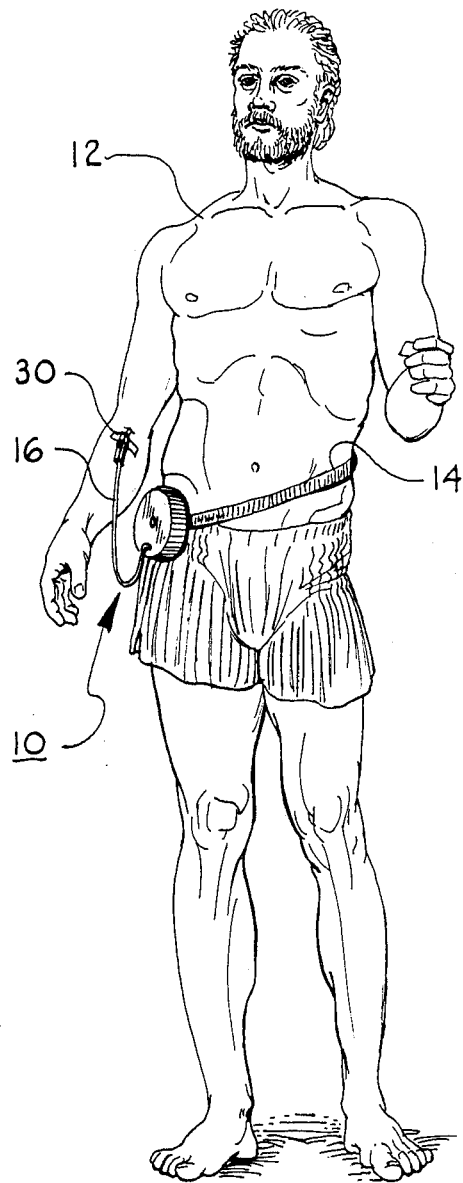
FIG. 1 shows the IV infusion device of the present invention attached to an ambulatory patient for the infusion of IV fluids to the patient.

Referring initially to FIG. 1, the disposable IV infusion device according to the present invention is shown in its operational environment and generally designated 10. Specifically, FIG. 1 shows that device 10 may be attached to an ambulatory patient 12 by any suitable means, such as a harness (not shown) or a belt 14. Although FIG. 1 shows device 10 infusing fluids via an IV line 16 into an arm of the patient 12, it will be appreciated that IV line 16 may be attached to the patient 12 wherever appropriate for the particular prescribed procedure.

Figure 2:
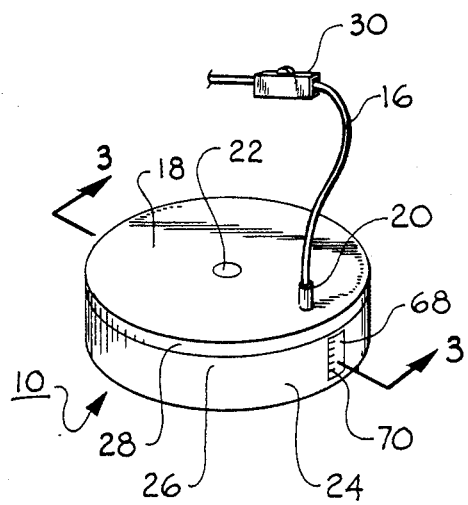
FIG. 2 is a perspective view of the IV infusion device of the present invention.

The external aspects and features of device 10 are perhaps best seen in FIG. 2 where it is shown that device 10 comprises a substantially disk-shaped cover plate 18 which is formed with a fluid port 20 and an air vent 22. FIG. 2 also shows that a cylindrical-shaped housing 24 has a periphery 26 which is joined to the edge 28 of cover plate 18. Additionally, a restrictor 30 is shown operatively connected to the flexible IV line 16 for controlling the flow of fluid through line 16. For purposes of the present invention, restrictor 30 may be a relatively simple device such as the well known roller clamp. Restrictor 30 may, however, be any device or apparatus well known in the pertinent art which selectively varies the cross-sectional area of IV line 16 to control fluid flow therethrough.

Figure 3A:
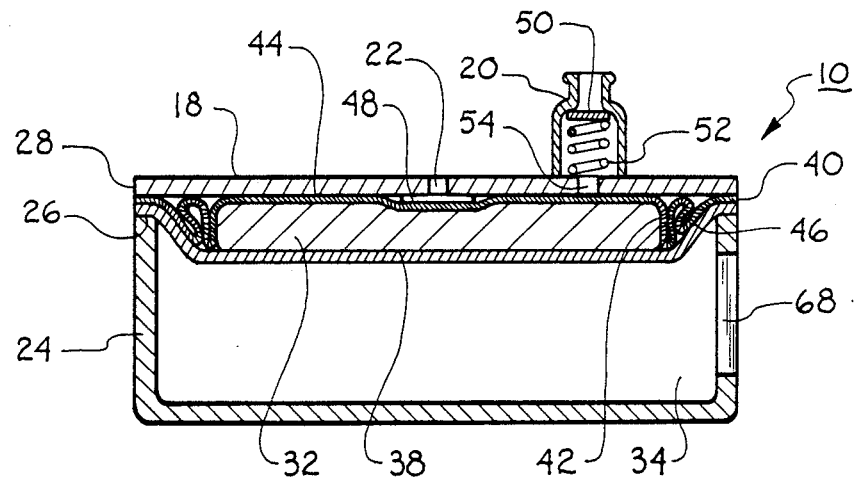
FIG. 3A is a cross-sectional view of the IV infusion device as seen along the line 3—3 in FIG. 2 with the cover plate and impeller plate in juxtaposed relationship.
Figure 3B:
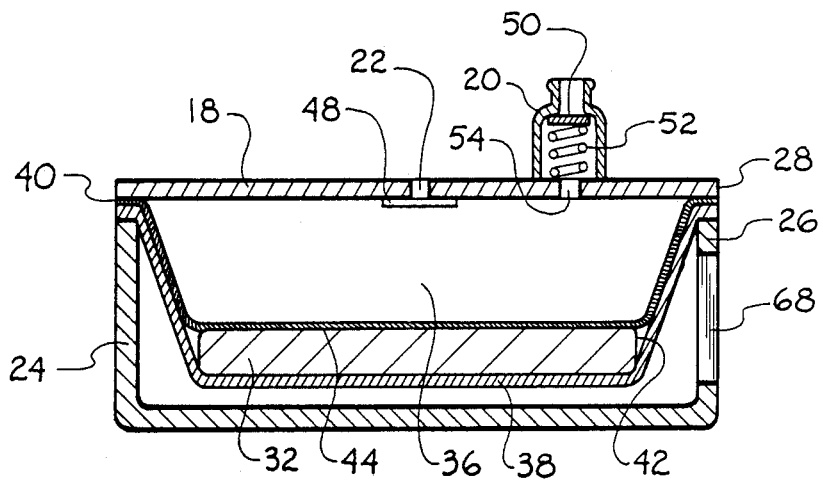
FIG. 3B is cross-sectional view of the IV infusion device of the present invention as shown in FIG. 3A with fluid injected between the cover plate and impeller plate to create a fluid chamber therebetween.

In FIGS. 3A and 3B the operative components of device 10 are shown to include a substantially disk-shaped impeller plate 32. As is best appreciated by cross referencing FIG. 3A with FIG. 3B, impeller plate 32 is received in opening 34 of housing 24 for movement between a position wherein impeller plate 32 is separated from cover plate 18 to establish a fluid chamber 36 therebetween (FIG. 3B), and a position wherein fluid chamber 36 has collapsed and impeller plate 32 is juxtaposed with cover plate 18 (FIG. 3A). The movement of impeller plate 32 relative to cover plate 18 between these positions results from the effect elastic membrane 38 has on the plates 18, 32. Specifically, membrane 38 is circular-shaped and, as shown in both FIGS. 3A and 3B, it has a peripheral edge 40 which is effectively attached to edge 28 of cover plate 18. More specifically, peripheral edge 40 of membrane 38 is held between edge 28 of cover plate 18 and the periphery 26 of housing 24. Furthermore, membrane 38 is positioned with impeller plate 32 placed between membrane 38 and cover plate 18. With this combination, impeller plate 32 is continuously urged into juxtaposition with cover plate 18 so long as membrane 38 is stretched. Importantly, for reasons to be subsequently discussed, membrane 38 is maintained in a stretched condition even when plates 18, 32 are juxtaposed as shown in FIG. 3A. Although membrane 38 has been previously described as being circular-shaped, and FIGS. 3A and 3B accordingly show membrane 38 covering impeller plate 32, it is to be appreciated that membrane 38 need only interconnect edge 28 of cover plate 18 with the edge 42 of impeller plate 32. Thus, if plates 18, 32 are disk-shaped, membrane 38 may be annular-shaped. Regardless of its configuration, however, membrane 38 needs to be made of a stretchable material, such as latex, which will impose a force on plates 18, 32 that urges the plates 18, 32 into juxtaposition.

A liner 44 made of a material such as polyethylene is provided in order to prevent the possible contamination of medical fluids in chamber 36 by membrane 38. As shown, liner 44 is disposed between cover plate 18 and impeller plate 32 and is held in this relationship by the interaction between edge 28 of cover plate 18 and the periphery 26 of housing 24. Also, because liner 44 is preferably nonresilient, a folded region 46 of liner 44 is provided to allow extension of liner 44 into a position as substantially shown in FIG. 3B.

In order to prevent infusion of gases into patient 12, a hydrophobic barrier 48 is positioned over air vent 22 to allow gases, but not liquid fluids, to escape from chamber 36 through port 20. On the other hand, liquid fluids, i.e. medical solutions, are injected into and expelled from chamber 36 through fluid port 20. In FIG. 3A, a typical fluid port 20 is seen to comprise an actuator valve 50 that is urged into a closed position by spring 52. By means well known in the pertinent art, valve 50 can be depressed to establish fluid communication through the passageway 54 of port 20 with chamber 36. With actuator valve 50 in its depressed position, fluid in chamber 36 can be expelled through port 20 and through its associated IV line 16 for infusion into patient 12.

OPERATION

In the operation of device 10, it is first placed on a horizontal surface (not shown) with air vent 22 positioned above impeller plate 32. A syringe or some other fluid container (not shown) is connected with port 20 to depress actuator valve 50 and inject fluid into chamber 36. Prior to injecting fluid into the device 10, it is to be noted that impeller plate 32 is juxtaposed with cover plate 18 as shown in FIG. 3A. Thus, to begin with, there is no established chamber 36. Nevertheless, even in this initial configuration, membrane 38 is stretched. This is so in order to achieve a substantially constant force from membrane 38 throughout its operational cycle.

Figure 4:
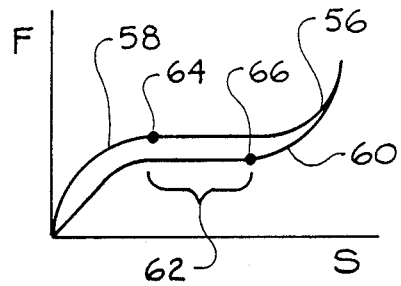
FIG. 4 is a model hysterisis curve showing the relationship between force and stretch length for a typical elastomeric membrane.

Referring for the moment to FIG. 4, it can be seen that the force (F) applied by a typical membrane 38 over its range of stretch (S) follows a hysterisis curve 56 which exhibits relationships between F and S during elongation 58 and contraction 60 that are substantially as shown. Importantly, during a contraction 60 there is a region 62 representing a range between approximately 30% and 70% of maximum stretch for membrane 38 in which the resultant force F is substantially constant. For purposes of the present invention, the operation of membrane 38 is preferably confined within this range. Consequently, as stated above, even in its initial position shown in FIG. 3A, membrane 38 is stretched into a condition generally represented by point 64 on curve 56.

As fluid is injected into chamber 36, any air which enters chamber 36 can escape through hydrophobic barrier 48 and air vent 22. Initially placing device 10 in a horizontal position as indicated above, helps the gases escape. Because of the hydrophobic barrier 48, however, the fluid injected into chamber 36 does not escape. Instead, it is forced into chamber 36 to distance impeller plate 32 from cover plate 18 into the configuration substantially as shown in FIG. 3B. In this configuration membrane 38 is stretched to a condition generally represented by point 66 on curve 56. Once the chamber 36 is filled, the syringe is removed, IV line 16 may then be connected to port 20, and device 10 can be used by patient 12, as desired. During operation, IV line 16 will need to include means well known in the art to depress actuator valve 50 to thereby allow fluid flow into IV line 16 from chamber 36. As fluid is expelled from chamber 36, membrane 38 will continue to urge or pull impeller plate 32 toward cover plate 18 under a substantially constant force F as indicated in FIG. 4. The actual rate of fluid flow from chamber 36 can then be controlled by patient 12, as desired, by the manipulation of restrictor 30.

It will be appreciated that the location of impeller plate 32 relative to cover plate 18 gives an indication of the amount of fluid in chamber 36. In order to observe the location of impeller plate 32, and thereby determine the amount of fluid to be infused, a window 68 is provided in housing 24 substantially located as shown in FIGS. 2, 3A and 3B. For purposes of the present invention, window 68 can be of any transparent material, such as clear plastic. Further, window 68 may be imprinted or marked with a scale 70, by any means well known in the art, to give more precise indications of the amount of fluid remaining in chamber 36.

While the particular disposable infusion device as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

We claim:

1. A portable device for infusing fluids to a patient which comprises:
    a first rigid plate having a fluid port, said first plate being circumscribed by an edge;
    a second rigid plate circumscribed by an edge;
    a stretched elastic membrane interconnecting and surrounding said respective edges for urging said first and second plates from a first configuration, in which said plates are separated to establish a fluid chamber therebetween, into a second configuration, wherein said plates are juxtaposed, to expel fluid from said chamber through said port to said patient, said membrane being disposed to urge said first and second plates between said first and second configurations with a substantially constant force;
    an IV line connected in fluid communication with said port; and
    a roller clamp associated with said IV line to control the flow of fluid from said chamber through said line.

2. A portable device for infusing fluids to a patient as recited in claim 1 wherein said membrane is made of an elastomeric material.

3. An ambulatory IV fluid infusion pump for infusing fluid to a patient which comprises:
    a cover plate bounded by an edge and formed with a fluid port;
    an impeller plate bounded by an edge;
    a stretched elastic membrane connecting said edge of said cover plate to said edge of said impeller plate for pulling said impeller plate toward said cover plate to expel fluid held therebetween by said membrane through said port to said patient, said membrane being surroundingly disposed around the respective said edges to pull said impeller plate toward said cover plate with a substantially constant force;
    a liner having a periphery, said liner being disposed between said cover plate and said impeller plate, and said periphery of said liner being attached to said cover plate to establish a fluid chamber between said liner and said cover plate, and
    an IV line connected in fluid communication with said port, and means associated with said IV line to control the flow of fluid from said chamber through said line.

* * * * *